United States Patent [19]
Venegas

[11] Patent Number: 5,854,423
[45] Date of Patent: Dec. 29, 1998

[54] APPARATUS AND METHOD FOR ASSESSMENT OF VISCO-ELASTICITY AND SHEAR ADHERENCE STRENGTH PROPERTIES OF BLOOD CLOTS

[76] Inventor: Jose G. Venegas, 12 Laurel Rd., Swampscott, Mass. 01907

[21] Appl. No.: 820,149

[22] Filed: Mar. 19, 1997

Related U.S. Application Data

[60] Provisional application No. 60/013,712 Mar. 20, 1996.
[51] Int. Cl.⁶ .......................... G01N 11/00; G01Y 33/86; C12Q 1/56
[52] U.S. Cl. ..................................... 073/64.41; 073/54.25; 073/64.42; 436/69; 422/73; 435/13
[58] Field of Search ............................... 73/54.01, 64.41, 73/54.25, 64.42, 61.45, 54.04, 54.09; 436/69; 422/73; 435/13

[56] References Cited

U.S. PATENT DOCUMENTS

| | | | |
|---|---|---|---|
| 3,667,286 | 6/1972 | Kaufman et al. | 73/59 |
| 3,719,075 | 3/1973 | Mandrona et al. | 73/54 |
| 3,720,097 | 3/1973 | Kron | 73/55 |
| 3,772,591 | 11/1973 | Louder et al. | 324/30 R |
| 3,839,901 | 10/1974 | Finkle et al. | 73/54 |
| 3,999,538 | 12/1976 | Philpot, Jr. | 128/2 G |
| 4,045,999 | 9/1977 | Palmer | 73/59 |
| 4,083,363 | 4/1978 | Philpot, Jr. | 128/2 G |
| 4,135,819 | 1/1979 | Schmid-Schönbein | 356/39 |
| 4,165,632 | 8/1979 | Weber et al. | 73/55 |
| 4,388,823 | 6/1983 | Garnaud et al. | 73/57 |
| 4,517,830 | 5/1985 | Gunn, deceased et al. | 73/57 |
| 4,554,821 | 11/1985 | Kiesewetter et al. | 73/55 |
| 4,558,589 | 12/1985 | Hemmes | 73/64.1 |

(List continued on next page.)

OTHER PUBLICATIONS

SIENCO®"Quality Instruments & Accessories", Hemostasis and Coagulation Analysis for Operating Room, Intensive Care and Critical Care plus Quality Instruments and Accessories for Stat, *Clinical, and Research Laboratories*.

Thurston et al., "Impedance of a Fibrin Clot in a Cylindrical Tube: Relation to Clot Permeability and and Viscoelasticity", *Biorheology*, vol. 32, No. 5, pp. 1–20, 1995.

Thurston, "Viscoelastic Properties of Blood and Blood Analogs", *Advances in Haemodynamics and Haemorheology*, vol. 1, ISBN 1–55938–634–7, pp. 1–34.

Seay et al., "Predictive Performance of Three Methods of Activated Clotting Time Measurement in Neonatal ECMO Patients",*ASAIO Journal*, 39–42, 1993.

(List continued on next page.)

*Primary Examiner*—Michael Brock
*Assistant Examiner*—Jay L. Politzer
*Attorney, Agent, or Firm*—Weingarten, Schurgin, Gagnebin & Hayes LLP

[57] ABSTRACT

The present invention, a thrombo visco-elastogram (TVE), measures the changes in blood elastic and viscous properties in the magnitude and phase of the hydro-dynamic impedance of a tubular blood sample as the thrombus is formed. The present invention is an apparatus and method for assessment of visco-elasticity and shear adherence strength properties of blood clots. An apparatus for practicing the invention includes a tubular conduit connected to a fluid-filled cylindrical chamber and a fluid-filled reservoir, a piezo-electric bender attached to the fluid-filled cylindrical chamber, which creates a volume variation in the fluid-filled cylindrical chamber, a fluid source capable of injecting a fluid into the tubular conduit, a blood source capable of injecting blood into the tubular conduit, and a microprocessor to supply a sinusoidal wave form or limited band frequency content signal to the piezo-electric bender and record and analyze resulting pressure signals. A method for practicing the invention measures the viscosity and elastic shear modulus of a blood sample over time obtaining the average and maximum viscosity and shear modulus for the blood sample as it clots, and further includes applying a forcing signal, which displaces the clotted blood sample, while measuring the applied pressure for clot dislodgement from the walls of the test section. The adherence strength properties of the blood clot are calculated.

20 Claims, 3 Drawing Sheets

U.S. PATENT DOCUMENTS

| | | | |
|---|---|---|---|
| 4,566,314 | 1/1986 | Thurston | 73/55 |
| 4,643,021 | 2/1987 | Mattout | 73/59 |
| 4,695,956 | 9/1987 | LeVeen et al. | 364/416 |
| 4,779,627 | 10/1988 | Kosasky | 128/738 |
| 4,780,418 | 10/1988 | Kratzer | 436/69 |
| 4,822,568 | 4/1989 | Tomita | 422/73 |
| 4,858,127 | 8/1989 | Kron et al. | 364/413.07 |
| 4,876,069 | 10/1989 | Jochimsen | 422/73 |
| 4,884,577 | 12/1989 | Merrill | 128/637 |
| 4,890,482 | 1/1990 | Maini | 73/55 |
| 4,947,678 | 8/1990 | Hori et al. | 73/54 |
| 4,964,297 | 10/1990 | Wechsler | 73/57 |
| 5,016,469 | 5/1991 | Henderson | 73/64.1 |
| 5,051,239 | 9/1991 | Von der Goltz | 422/73 |
| 5,138,872 | 8/1992 | Henderson | 73/64.41 |
| 5,139,741 | 8/1992 | Hagiawara | 422/48 |
| 5,222,497 | 6/1993 | Ono | 128/637 |
| 5,257,529 | 11/1993 | Tangiuchi et al. | 73/54.09 |
| 5,272,912 | 12/1993 | Katsuzaki | 73/54.08 |
| 5,293,772 | 3/1994 | Carr, Jr. | 73/64.41 |
| 5,302,348 | 4/1994 | Cusak et al. | 422/73 |
| 5,315,863 | 5/1994 | Cowper | 73/54.09 |

OTHER PUBLICATIONS

Zuckerman et al., "Comparison of Thrombelastography with Common Coagulation Tests", *Thromb Haemostas*(Stuttgart) 46(4) 752–756, 1981.

Sonoclot® Coagulation & Platelet Function Analyzer For In Vitro Diagnostic Use–An Overview Copyright© 1994–1996 Sienco, Inc., pp. 1–14.

Hett et al., "Sonoclot Analysis", British Journal of Anaesthesia, 75:771–776,1995.

Mallett et al., "Thrombelastography", British Journal of Anaesthesia, 69:307–313, 1992.

Tuman et al., "Comparison of Viscoelastic Measures of Coagulation after Cardiopulmonary Bypass", ANESTH ANALG, 69:69–75, 1989.

The Vilastic 3–Viscoelasticty Analyzer, 4 pages.

Henderson et al., "A New Method for the Analysis of Blood and Plasma Coagulation", ISA, Paper No. 93–013, pp. 95–102, 1993.

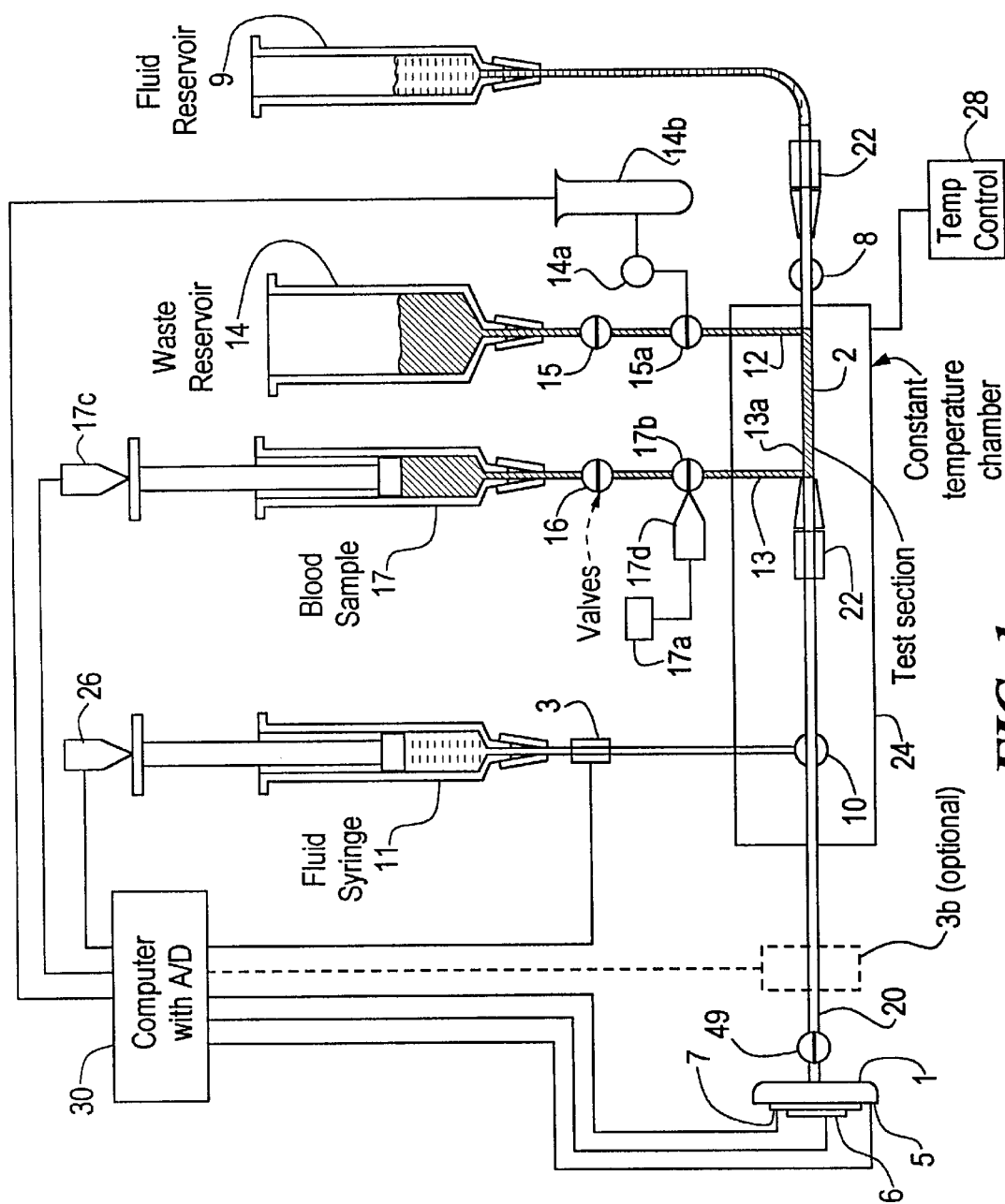
FIG. 1
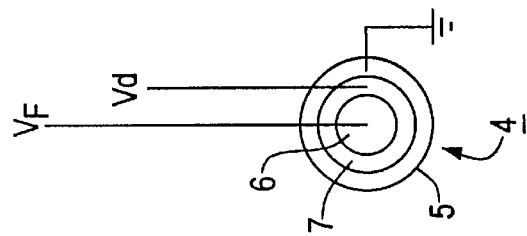

APPARATUS AND METHOD FOR ASSESSMENT OF VISCO-ELASTICITY AND SHEAR ADHERENCE STRENGTH PROPERTIES OF BLOOD CLOTS

CROSS-REFERENCE TO RELATED APPLICATIONS

The instant invention is a utility application of co-pending Provisional Patent Application Serial No. 60/013,712, filed Mar. 20, 1996.

FIELD OF THE INVENTION

The present invention relates to an apparatus and a method for clinical assessment of blood coagulation.

BACKGROUND OF THE INVENTION

The primary function of the coagulation system is to stop bleeding from ruptured blood vessels and capillaries in a wound. This system consists of an extremely complex combination of checks and balances. During a bleeding episode, blood is exposed to extra vascular tissues, triggering a cascade of events that ultimately results in a phase transformation of the blood from a fluid into a gel (thrombus). This thrombus attaches to the surrounding tissues and serves as a temporary plug for the ruptured vessel, thus preventing further blood loss. A thrombus therefore must not only be created rapidly, but it must also be strong and well attached to the vessel wall and surrounding tissues. In addition it should remain strong and attached until the wound is repaired by slower but more permanent mechanisms. A defect in any one of these qualities may prevent effective hemostasis.

The clinical assessment of clotting function has long been recognized to be important in the management of surgical patients. Preoperatively, the assessment of the clotting function is utilized as a predictor of risk of patient bleeding, allowing advanced preparation of blood components. Perioperative monitoring of clotting function is also important because coagulopathies can be induced by hemodilution of procoagulants, fibrinogen and platelets, by consumption of coagulation factors during surgical procedures, or by cardiopulmonary bypass. Standard laboratory clotting tests take from 25–60 minutes and do not accurately predict the result of potential pharmacological or blood replacement therapies. Real-time assessment of clotting function is needed not only to evaluate the result of therapeutic interventions, but also to test and optimize, a priori, the treatment choice and dosage.

Post operative assessment of clotting function is also crucial. For example, 3–5% of cardiopulmonary bypass patients require surgical re-examination to stop bleeding. Prompt assessment of clotting function could rule out coagulopathy as the cause of bleeding, thus avoiding unnecessary surgery that adds to patient morbidity and treatment costs.

Several tests of coagulation are routinely utilized to assess the complicated cascade of events leading to blood clot formation and test for the presence of abnormalities or inhibitors of this process. Among these tests are platelet count (PLT), prothrombin time (PT), partial thromboplastin time (aPTT), activated clotting time (ACT), fibrinogen level (FIB) and fibrinogen degradation product concentrations, aPTT can also be use to assess the degree of anticoagulation resulting from heparin administration, while PT can indicate the level of anticoagulation produced by warfarin administration.

In the bleeding patient, results from these tests are generally used to determine which standard transfusion medicine interventions might be appropriate for the clotting disorder at hand. For example, elevated PTT usually indicates heparin excess and protamine can be administered; elevated PT usually indicates inadequate levels of humoral clotting factors and fresh frozen plasma is required; reduced platelet count can be related to ongoing consumption and is treated with platelet concentrate administration.

Although these tests are appropriate in the management of relatively stable medical patients, they often do not provide results within a clinically appropriate time frame in acute hemorrhage patients. In many cases, the data have become irrelevant by the time it is received and clinicians are forced to use preemptive therapy, exposing patients to multiple and possibly unnecessary donor blood units. More importantly, these tests give little or no information about the appropriate use of pharmacological alternatives to transfusion such as aprotinin and epsilonamino-caproic acid. Furthermore, the standard tests fail to predict the risk of postoperative bleeding, since they do not assess the mechanical strength of the forming clots.

Bleeding time, the time it takes for bleeding to stop from a small incision, is a parameter which has been used to assess overall blood clotting. This parameter, unfortunately, is highly dependent on the size and location of the vessels affected by incision and of the physiological variables such as arterial and venous blood pressures. Bleeding time, is therefore a rather imprecise index of overall clotting function. One prior art method of assessing bleeding time is the manual method. This method requires the continuous presence of a technician or nurse to constantly wipe out the blood from the skin incision to determine, in a crude way the duration of bleeding. This requirement of constant dedication of the medical personnel makes the test costly and subjective.

Standard clotting and bleeding time tests typically measure the period of time required for the thrombus, or one of its components, to reach an arbitrarily defined state. These tests, therefore, give information about the kinetics of clotting, but do not provide quantitative information about the final strength of the resulting thrombus that could be used to predict hemostasis under more general conditions.

An indirect method of assessing whole blood coagulation is used is thromboelastography (TEG). This method follows the changes in elastic properties of a blood clot from the time the first fibrin strands are formed to the completion of the clot formation and then as the clot dissolves during fibrinolysis. This method, however, has poor reproducibility of derived parameters due to the freedom in the volume and geometry of the blood sample that is being tested and the elaborate nature of the test. In short, TEG's quantitative validity strongly depends on the operator's technique.

The SONOCLOT is another device used to assess changes in mechanical properties of blood as it clots. This method is similar to the TEG in that it measures the changes in the dynamic response of a forming clot following the application of an oscillatory perturbation. As with TEG, the quantitative validity of the test strongly depends on the operator's technique.

Furthermore, both TEG and SONOCLOT have a substantial degree of inaccuracy and as much as 15% to 33% of false positive tests for predicting the cause of postoperative hemorrhage are given by these devices. These tests, although better than routine clotting tests, can result in unnecessary surgical re-operation of a patient.

SUMMARY OF THE INVENTION

The present invention and improvements in a device known as a thrombo visco-elastogram (TVE), avoids the problems of the prior art by measuring the changes in blood elastic and viscous properties in the magnitude and phase of the hydro-dynamic impedance of a tubular blood sample as the thrombus is formed.

In an exemplary embodiment, the apparatus of the present invention includes a tubular conduit having two ends, and multiple branching tubes. A fluid-filled cylindrical chamber is connected to one end of the tubular conduit, a fluid-filled reservoir is connected to the other end of the tubular conduit. A piezo-electric bender is attached to the fluid-filled cylindrical chamber and deforms in response to a voltage polarity which causes a corresponding volume variation in the fluid-filled cylindrical chamber. A fluid source capable of injecting a fluid into one of the multiple branching tubes of the tubular conduit is also provided, along with a blood source capable of injecting blood into another one of the multiple branching tubes of the tubular conduit. A microprocessor is used to supply a sinusoidal wave form or limited band frequency content signal to the piezo-electric bender, and the microprocessor records and analyzes electric signals, including displacement and pressure signal values.

The method of the present invention measures the viscosity and elastic shear modulus of a blood sample over time obtaining the rate of change and maximum viscosity and shear modulus for the blood sample as it clots. The next step applies a ramping pressure across the axis of a test section of a tube containing the clotted blood sample, until the clot is dislodged from the walls of the test section, and the shear adherence strength properties of the blood clot are calculated from the maximum pressure supported by the clot before it is dislodged.

Additional features of the present invention include the ability to run multiple blood samples sequentially.

BRIEF DESCRIPTION OF THE DRAWINGS

The invention will be more fully understood by reference to the following detailed description when considered in conjunction with the accompanying drawings, in which:

FIG. 1 is a diagram of an embodiment of an apparatus of the present invention;

DETAILED DESCRIPTION OF THE INVENTION

Figure 2:
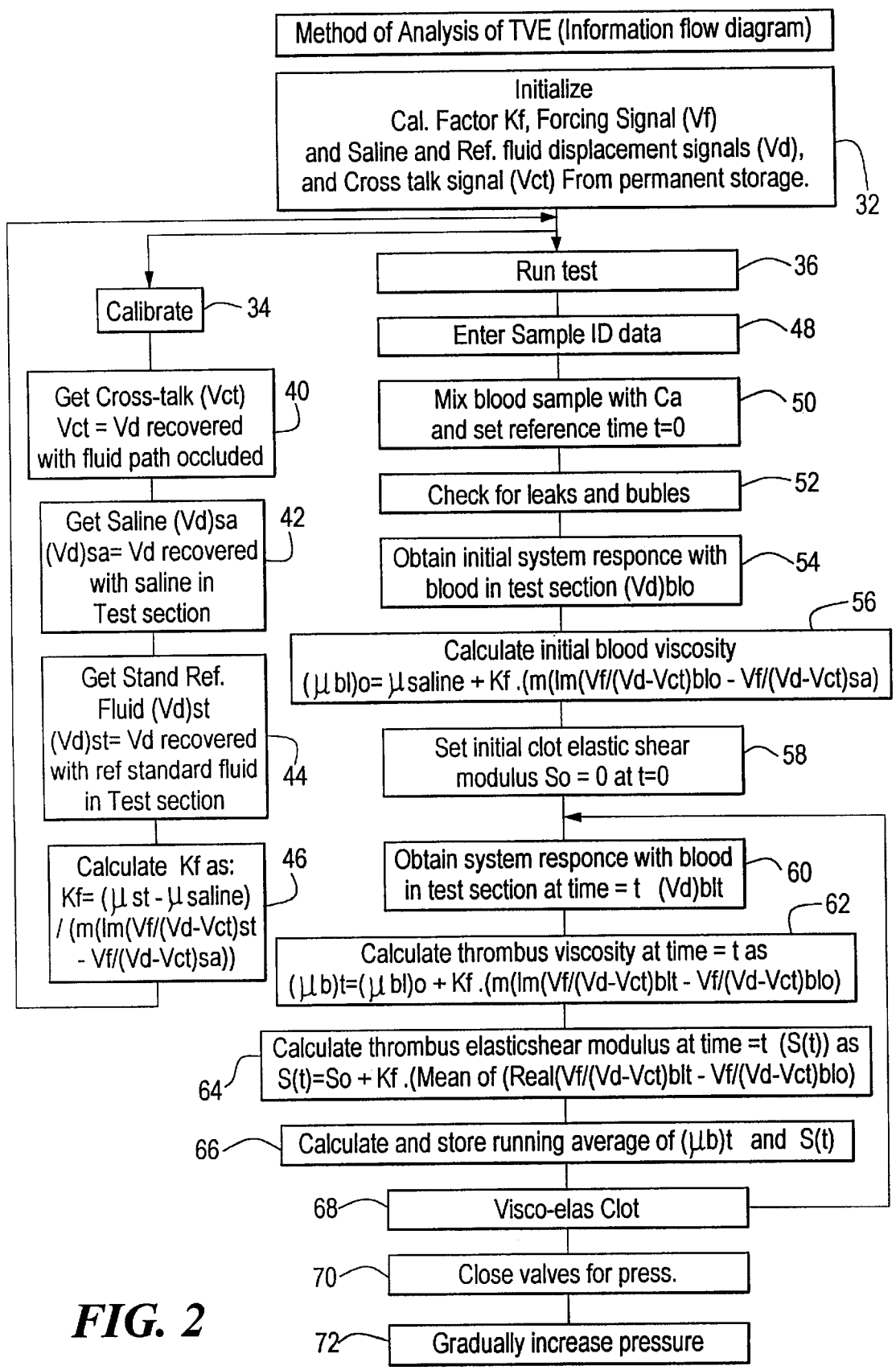
FIG. 2 is a flow diagram of an embodiment of a method of analysis using an embodiment of the invention shown in FIG. 1.

Apparatus and method for assessment of visco-elasticity and shear adherence strength properties of blood clots are described below and by referring to FIGS. 1, 2 and 3.

The apparatus of FIG. 1 provides instrumentation for creating a blood clot and evaluating its viscosity and elasticity as it is formed using a bender having ground electrode 5, drive electrode 6, and sensor electrode 7 attached to a fluid-filled chamber 1. An end view of the chamber showing the bender is shown at 4. A bender of known design is shown in U.S. Pat. No. 5,026,348, incorporated herein by reference. The chamber 1 communicates past a shutoff valve 49 through a tube 20, to a fluid or air heated chamber 24, where pressurization of the tube 20 from a fluid-filled source such as a syringe 11 (or other pressure source) is achieved from a plunger drive 26, forcing fluid into tube 20 to pressurize a clot in a confined, well-defined cylindrical test section 2 with thrombogenic inert surface, such as glass or collagen coated surface. The chamber 24 is temperature controlled at body temperature by control 28 to typically ±0.1° C. The fluid in syringe 11 and tube 20 is immiscible and inert in exposure to blood. PERFLUBRON of Alliance Pharmaceutical is one such material.

A saline or other wash source 17a is connected alternatively with blood from sample syringe 17 in blood input line 13 via valves 17b and 16 allowing saline or blood to pass into test section 2. A valve 15a is provided in the waste stream 12 from section 2 and is connected alternatively via a pump 14a to a waste reservoir 14b. Alternatively, a valve 15 and waste reservoir 14 under vacuum can be used. Syringe 17 can be replaced by a blood reservoir and pump.

A saline, oil or immiscible and inert fluid is provided in reservoir 9 to confine blood in section 2.

The bender output is taken at electrode 7 and has, relative to the driving signal $V_f$ from computer 30, real or in phase components, Re, and imaginary or quadrature components Im, determined by synchronous detection either by analog or digital means.

FIG. 2 shows a flow diagram of one possible method of analysis for thrombus-visco-elasticity and clot shear attachment strength as determined using the apparatus of FIG. 1. FIG. 2 and the following description will be more fully understood by reference to Table 1.

TABLE I

GLOSSARY OF VARIABLES AND ABBREVIATIONS FOR FIG. 2

| | |
|---|---|
| $K_f$ = | Calibration Factor |
| $V_f$ = | Force Signal |
| $V_{ct}$ = | Cross Talk Signal |
| $V_d$ = | Displacement Signal from Bender |
| sa = | Saline |
| st = | Standard Reference Fluid |
| blo = | Blood in Test Section |
| blt = | Blood in Test Section at a time t |
| $\mu$ = | Viscosity |
| m = | Slope |
| t = | Time |
| f = | Frequency |
| Im = | Imaginary Component |
| Re = | Real Component |
| S = | Shear Modulus of elasticity |
| S (t) = | Thrombus Shear Modulus of elasticity at time t |
| $\mu_b$ (t) = | Thrombus viscosity at time t |

The method of FIG. 2 begins with an initialization step 32. The initialization step involves accessing from records in computer 30, a calibration factor ($K_f$), a forcing signal value ($V_f$), fluid displacement signals for saline and a standard reference fluid ($V_d$), and a cross-talk signal ($V_{ct}$) if they exist. If they do not exist, a routine described below determines their value.

FIG. 2 shows two subroutines, calibration routine 34 where $K_f$ is initially determined and run routine 36 of running the blood test for visco-elasticity and shear attachment strength.

The method of calibration which calculates $K_f$ involves obtaining a cross talk value $V_{ct}$ in step 40 by occluding, with valve 49, the opening of chamber 1, and exciting the bender with the forcing signal ($V_f$) while recording the displacement signal ($V_d$). Since actual bender displacement is prevented by the closure of valve 49, the recorded voltage ($V_d$) will correspond to a value representing cross talk between forcing and displacement electrodes in the bender. Such cross talk is mostly caused by mechanical effects within the respective electrode covered areas of the piezoelectric crystal and is close to 180° out of phase with the exciting signal ($V_f$) at all frequencies of interest (1–50 Hz). Steps 42 and 44 then establish the bender signals ($V_d$) for saline and a second reference fluid in test section 2 using the syringe 17 and reservoir 14 as source and pump for applying the fluids to section 2. Then in step 46, by taking the difference in known fluid viscosities ($\mu$) divided by the slope (m) of a plot of the imaginary component (Im) versus frequency (f) of the difference in transfer functions ($V_f/(V_d-V_{ct})$) of the dynamic response with the standard fluid (st) in the test section minus the dynamic response with a second fluid such as saline (sa) in the test section, $K_f$ is determined.

The value of $K_f$ is then used in the actual test run 36 flow diagram to calculate the time progression of the thrombus elastic shear modulus (S(t)) and viscosity (($\mu_b$)t) at time (t). The blood visco-elasticity test is begun in step 48 using the calibration data, by placing a citrated blood sample in syringe 17. The blood sample is then mixed with calcium chloride to allow the initiation of the clotting cascade in step 50 and a reference time is set at t=0. The next step 51 includes the introduction of the blood sample into the test section by closing valves 8 and 10 (valves 17b and 15a set for blood flow), and opening valves 15 and 16 and injection from syringe 17, optionally using pusher 17c, or pump 14a, under computer 30 control. After the test section 2 is completely filled with the blood sample, the valves 15 and 16 shown in FIG. 1, leading to the blood sample chamber and the waste reservoir are closed. Step 52 includes checking for air bubbles or leaks by closing valve 8 and connecting the test section 2 with chamber 1 through valves 10 and 49. At this point, the bender is excited with a chirped signal, pseudo-random noise, or several such as 5 or 10 discrete known frequencies with frequency content of typically 1–50 Hz ($V_f$) and the displacement signal ($V_d$) from the bender is acquired by computer 30. The displacement ($V_d$) signal is then compared with stored ($V_{ct}$) and if equal within a very small margin of difference, the absence of bubbles or leaks is confirmed. A greater difference between ($V_{ct}$) and ($V_d$) at this point will signify the presence of a leak or air bubbles and the operator will be alerted. In step 54, valve 8 is opened and initial system responses ($V_d$)$_{blo}$ are then obtained with the blood in the test section 2.

The initial blood viscosity is calculated by the formula shown in the following step 56 of the run test steps. After the initial viscosity measurements are obtained, the elastic shear modulus ($S_o$) is set to 0 in step 58 at time t=0.

The process then runs in a loop through steps 60, 62, 64 and 66 through a step 68, returning to step 60.

Step 60 acquires the response ($V_d$) with blood at a given t, indexed with each loop passage. Step 62 calculates the viscosity at that t, while step 64 calculates the shear modulus of elasticity at the same t. These values are stored at step 66 before looping back to step 60 for sampling ($V_d$) at the next t. The wave form of the drive signal ($V_f$) is the same chirped, pseudo-random noise or discrete frequency with a frequency content of 1–50 Hz used in the calibration steps. While the system is shown to use the driving ($V_f$) and displacements ($V_d$) signals; any two of these plus the signal from sensor 20 can be used in equations for that purpose.

After a maximal shear modulus of elasticity is reached, the test proceeds through step 68 to step 70 for conducting a popping test on the clot. The syringe 11 is then pressurized with valve 49 closed, valve 10 open and valves 16 and 15 closed. Driver 26 operates to increase the pressure of fluid in line 20 as applied to Section 2. As the resulting pressure increases in step 72, pressure is measured by pressure transducer 3 and/or alternative or optional pressure transducer 3b and received by computer 30. When the pressure overcomes the attachment strength of the clot to the test section walls, as evidenced by a maximum in the value of the pressure $P_{max}$ followed by a fastfall, the shear strength property of the clot's adherence to the walls of the test section 2 can be assessed knowing $P_{max}$ and the geometry of test section 2 to which the clot attaches according to:

$$(P_{max}) \cdot (\pi R^2) = (\tau_{max}) \cdot (2\pi RL)$$
$$\tau_{max} = \frac{P_{max}R}{2L}$$

Where R and L are the section 2 radius and length respectively and $\tau_{max}$ is a measure of clot adherence shear strength.

The reservoir 9 may include saline or an immiscible and inert fluid including oil. With a large cross-sectional area of reservoir 9, surface tension effects between air and the fluid can be ignored but if the cross-sectional area is small, surface tension forces at the air-fluid interface need to be accounted for in the calculation.

Between tests, the valves 15a and 17b are positioned to flush test section 2 with a cleaning agent and then with saline using pump 14a. The entire system can be flushed of blood by use of a pump 17d to flow saline through syringe 17 and flush out line 12 to the couplings where reservoir 14 and syringe 17 are installed.

Figure 3:
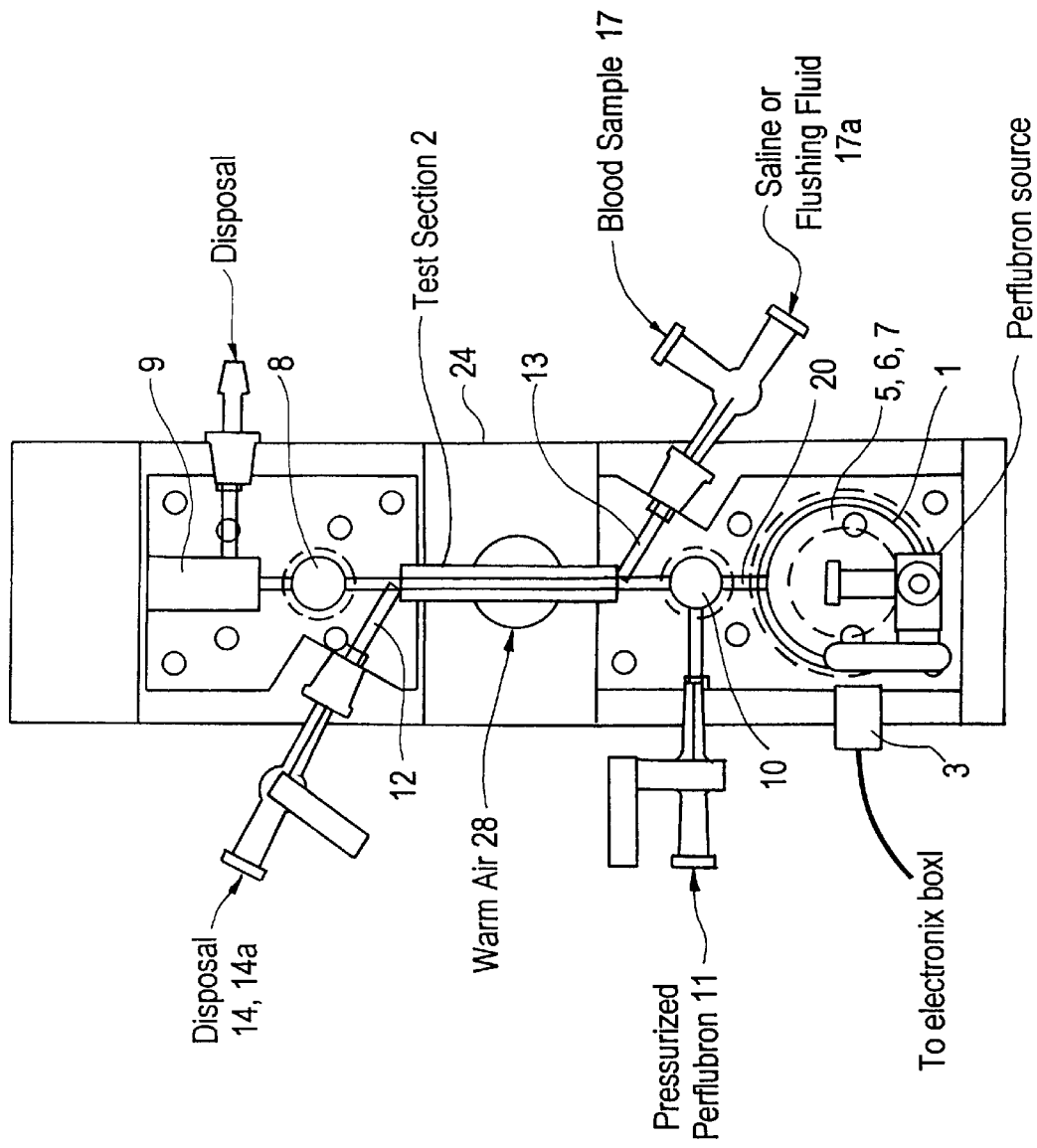
FIG. 3 is a diagram of another embodiment of an apparatus of the present invention.

FIG. 3 shows a modularized, plastic version of the system more suitable for automation where like parts to FIG. 1 are labelled with the same numbers. FIG. 3, including as desired, the bender, can be readily fabricated as a disposable unit. Multiple apparatuses, as shown in FIG. 3, can be configured to run multiple tests sequentially.

The invention can be further utilized for measuring shear adherence strength of other polymerzable or gellable fluids, such as paint, resins and epoxies.

Although the invention has been shown and described with respect to exemplary embodiments thereof, various other changes, omissions and additions and form in detail thereof, may be made therein without departing from the spirit and scope of the invention. Accordingly, the drawings and detailed description of the invention are to be regarded as illustrative in nature and not as restrictive.

What is claimed is:

1. An apparatus for assessment of visco-elasticity and/or shear adherence strength properties of blood as it clots, said apparatus comprising:

a tubular conduit having a first section, a second section, and an intermediate zone therebetween for blood under test;

a fluid chamber connected to said first section of said tubular conduit and in fluid communication with said intermediate zone;

a piezo-electric bender attached to said fluid chamber, said bender deformable in response to a signal to cause a volume variation in said fluid chamber, which causes a pressure variation and displacement effect in fluid in said tubular conduit including said intermediate zone, the shape and amplitude of which effect when detected reflect clotting properties in blood in said intermediate zone.

2. The apparatus of claim 1 wherein the displacement and/or pressure associated with said effect is detected.

3. The apparatus of claim 1, further comprising:
a signal-generator for supplying a sinusoidal waveform of limited band frequencies to said piezo-electric bender.

4. The apparatus of claim 2, wherein a pressure sensor responds to said pressure effect reflecting a hydrodynamic impedance within blood in said intermediate zone, whereby changes in said hydrodynamic impedance corresponding to changes in visco-elastic properties of blood in said intermediate zone are sensed.

5. The apparatus of claim 1, wherein said tubular conduit includes blood and non-blood fluid inlets and outlets respectively associated with the first and second section.

6. The apparatus of claim 1, further comprising a pressure transducer in said first section.

7. The apparatus of claim 5, further comprising a wash inlet in communication with said tubular conduit, said wash inlet for supplying a liquid to said tubular conduit to cleanse said tubular conduit intermediate zone.

8. The apparatus of claim 1, including a microprocessor to receive a signal representing said effect over a time interval during progressive clotting of blood in said intermediate zone.

9. The apparatus of claim 1 further including a source of ramped pressure to said conduit to cause shear failure popping of a clot in said intermediate zone; and
said effect representing signal includes a pressure signal rising to a peak before clot shear failure.

10. The apparatus of claim 1, wherein said tubular conduit has an inner surface coating with clot attachment properties equivalent to those of physiologic substances.

11. A method for detecting blood thrombus properties comprising the steps of:
applying to a bolus of blood in a conduit a fluid force varying at two or more frequencies and inducing an effect manifested in fluid pressure and displacement in said conduit wherein a piezo-electric bender is attached to a fluid chamber connected to said conduit, said bender deformable in response to a signal to cause a volume variation in said fluid chamber, which causes a pressure variation and displacement effect in fluid in said conduit, the shape and amplitude of which effect when detected reflect clotting properties in blood in said conduit;
sensing said effect in said conduit in response to the applied force;
analyzing in the frequency domain a transfer function between the applied force and the sensed effect at said two or more frequencies over time for changes in real and imaginary components of said transfer function representing changes in viscosity and shear modulus of elasticity of the blood in said conduit.

12. A method of assessing attachment shear strength including the steps of:
providing a bolus of blood in a conduit;
forming a clot with stable mechanical properties from said bolus of blood within said conduit;
applying a gradually increasing pressure to said clot in said conduit;
measuring a maximum pressure in said conduit until detachment of said clot from walls of said conduit; and
calculating an attachment shear strength from the maximum pressure measurement.

13. The method of claim 11, wherein the step of analyzing comprises the steps of:

obtaining a cross-talk signal by exciting a bender in a chamber, connected to said conduit with a forcing signal and sensing a resulting displacement signal from said sensor while said conduit is occluded, obtaining calibration signals by exciting said bender with said forcing signal and sensing the resulting displacement signals for at least two fluids of differing known viscosities;
calculating a calibration factor as a function of the known fluid viscosity for said fluids, said forcing signal, said cross-talk signal and said calibration signals; and
analyzing the sensed effect for change in viscosity and elasticity of blood as a function of said calibration factor.

14. The method of claim 11 including the steps of calculating by a microprocessor changes in blood viscosity over time as a function of said sensing effect over time and said calibration factor with a bolus of blood in said conduit.

15. The method of claim 14, wherein the step of analyzing for shear modulus of elasticity comprises the steps of:
obtaining an initial displacement signal by applying a forcing signal to said conduit and recording said resulting displacement signal;
calculating by microprocessor the shear modulus of elasticity of a bolus of blood as a function of said forcing signal and said calibration factor; and
wherein the step of analyzing is repeated over time during which said bolus of blood clots.

16. A method for assessment of visco-elasticity and shear adherence strength properties of blood clots, said method comprising the steps of:
calibrating a blood test system to establish a calibration factor using a forcing signal, a fluid displacement signal for a first reference fluid within a conduit, a fluid displacement signal for a second reference fluid within said conduit, a cross-talk signal for a bender in fluid communicating with said conduit;
mixing a sample of citrated blood with a clotting activation agent such as calcium chloride to initiate a clotting cascade;
supplying and confining said blood sample to a test section of said conduit;
applying said forcing signal to said bender in fluid communication with said conduit;
obtaining an initial viscosity as a function of said forcing signal and said cross talk signal for a fluid in said test section;
repeatedly obtaining viscosity and thrombus elastic shear modulus values of a blood sample in said test section while said blood sample coagulates and forms a blood clot attached to the walls of said test section;
calculating and storing peak viscosity and elastic shear modulus values of said blood during clotting;
gradually increasing pressure across said blood clot in said test section and measuring a pressure in said conduit until the detachment of a blood clot from walls of said test section; and
calculating and storing peak viscosity and rate of change of viscosity and peak elastic shear modulus and peak rate of change of elastic shear modulus as a function of the times of their occurrence relative to the addition of the clotting activation agent before detachment.

17. The method of claim 16, wherein the step of calibrating comprises the steps of:
obtaining said cross-talk signal by occluding the opening of a fluid-filled chamber having a bender, and exciting said bender with a forcing signal while recording the displacement signal which represents cross-talk between forcing and displacement electrodes in said bender; and calculating by microprocessor said calibration factor as a function of known fluid viscosities from said reference fluids, said forcing signal, said displacement signal and said cross-talk signal.

18. The method of claim 16, further comprising the steps of:

flushing said test section with a cleaning agent; and flushing said test section with an immiscible and inert fluid.

19. A method for obtaining visco-elastic properties of blood confined in a conduit and pressured by a bender comprising checking said conduit for leaks and air bubbles by applying a known pressure signal to said bender and measuring a resulting displacement signal while said conduit is occluded;

comparing said displacement signal to a bender cross-talk signal, to generate an error indication signal if said displacement signal and said cross-talk signal are not substantially equal.

20. A method for obtaining visco-elastic properties of blood confined to a conduit in fluid communicating with pressure generator comprising the step of obtaining a calibration factor for said conduit and a bender with at least two reference fluids in said conduit and pressure generator; and measuring visco-elasticity changes over time for blood in said conduit as a function of pressure applied to said conduit by said generator and said calibration factor.

* * * * *